US012053603B2

United States Patent
Shamim et al.

(10) Patent No.: US 12,053,603 B2
(45) Date of Patent: Aug. 6, 2024

(54) REMOTE DETERMINATION OF ULTRASONIC CSF FLOWRATE IN VP SHUNT VIA MACHINE LEARNING AND ULTRASOUND FREQUENCY MATCHING

(71) Applicant: The Aga Khan University, Karachi (PK)

(72) Inventors: Muhammad Shahzad Shamim, Karachi (PK); Saleem Sayani, Wynnewood, PA (US); Syed Sarmad Bukhari, Hayatabad (PK); Muhammad Abdul Muqeet, Karachi (PK); Hafiz Imtiaz Ahmed, Karachi (PK)

(73) Assignee: The Aga Khan University, Karachi (PK)

( * ) Notice: Subject to any disclaimer, the term of this patent is extended or adjusted under 35 U.S.C. 154(b) by 191 days.

(21) Appl. No.: 17/462,641

(22) Filed: Aug. 31, 2021

(65) Prior Publication Data
US 2023/0001164 A1    Jan. 5, 2023

(30) Foreign Application Priority Data

Jul. 1, 2021    (PK) ...................................... 492/2021

(51) Int. Cl.
  *A61M 27/00*    (2006.01)
  *A61B 5/00*    (2006.01)
  (Continued)

(52) U.S. Cl.
  CPC ......... *A61M 27/006* (2013.01); *A61B 5/0086* (2013.01); *A61B 5/031* (2013.01);
  (Continued)

(58) Field of Classification Search
  CPC ........ A61M 27/006; A61M 2205/3313; A61M 2205/3334; A61M 2205/3368;
  (Continued)

(56) References Cited

U.S. PATENT DOCUMENTS

2006/0020239 A1    1/2006 Geiger et al.
2008/0214951 A1    9/2008 Fritz et al.
(Continued)

OTHER PUBLICATIONS

Muscas et al (Development of machine learning models to prognosticate chronic shunt-dependent hydrocephalus after aneurysmal subarachnoid hemorrhage; Vascular Neurosurgery—Other Open access Published: Jul. 8, 2020 vol. 162, pp. 3093-3105 ( 2020) (Year: 2020).*

(Continued)

*Primary Examiner* — Serkan Akar
(74) *Attorney, Agent, or Firm* — Fish & Richardson P.C.

(57) ABSTRACT

A method for monitoring a flowrate of cerebrospinal fluid (CSF) in a ventriculo-peritoneal (VP) shunt implanted in a human patient includes: (i) receiving, at a device external to the human patient, data sensed by a plurality of sensors within the device and positioned relative to the VP shunt to drain excess cerebrospinal fluid from the human patient's brain; (2) determining, by the device and based on the sensed data, a rate of flow of the CSF in the VP shunt; and (3) transmitting (e.g., wirelessly), by the device, data indicating the rate of flow to a computing server.

13 Claims, 15 Drawing Sheets

(51) Int. Cl.
*A61B 5/03* (2006.01)
*G16H 20/40* (2018.01)
*G16H 40/60* (2018.01)

(52) U.S. Cl.
CPC ............ *A61B 5/032* (2013.01); *A61B 5/6847* (2013.01); *G16H 20/40* (2018.01); *G16H 40/60* (2018.01); *A61M 2205/3313* (2013.01); *A61M 2205/3334* (2013.01); *A61M 2205/3368* (2013.01); *A61M 2205/3375* (2013.01); *A61M 2205/3553* (2013.01); *A61M 2205/3584* (2013.01); *G01N 2291/02466* (2013.01)

(58) Field of Classification Search
CPC .. A61M 2205/3375; A61M 2205/3553; A61M 2205/3584; A61B 5/0086; A61B 5/031; A61B 5/032; A61B 5/6847; G16H 20/40; G16H 40/60; G16H 50/30; G16H 50/20; G01N 2291/02466
See application file for complete search history.

(56) References Cited

U.S. PATENT DOCUMENTS

| | | |
|---|---|---|
| 2011/0054382 A1 | 3/2011 | Fritz et al. |
| 2011/0275976 A1 | 11/2011 | Negre et al. |
| 2013/0109998 A1 | 5/2013 | Swoboda et al. |
| 2013/0226066 A1 | 8/2013 | Liu |
| 2014/0005589 A1 | 1/2014 | Fritz et al. |
| 2014/0303455 A1 | 10/2014 | Shachar et al. |
| 2015/0119719 A1 | 4/2015 | Sharma et al. |
| 2015/0201882 A1* | 7/2015 | Swoboda ............. A61B 5/4058 600/549 |
| 2017/0224968 A1 | 8/2017 | Utz et al. |
| 2019/0285500 A1* | 9/2019 | Budgett ................... A61B 5/03 |
| 2022/0355086 A1* | 11/2022 | Alshareef ............... G01F 1/663 |

OTHER PUBLICATIONS

International Search Report and Written Opinion in International Application No. PCT/US2022/073381, dated Sep. 30, 2022, 14 pages.

Rajasekaran et al., "Mechanism for measurement of flow rate of cerebrospinal fluid in hydrocephalus shunts," Annual Int. Conference IEEE Eng. Med. Biol. Soc., Aug. 26, 2014, 4 pages.

* cited by examiner

REMOTE DETERMINATION OF ULTRASONIC CSF FLOWRATE IN VP SHUNT VIA MACHINE LEARNING AND ULTRASOUND FREQUENCY MATCHING

RELATED APPLICATION

This application claims priority to Pakistan Patent Application No. 492/2021, entitled "Remote Determination of CSF Flowrate in VP Shunt," filed on Jul. 1, 2021, the entire contents of which are incorporated herein by reference.

TECHNICAL FIELD

The subject matter described herein relates to remote detection of flowrate of cerebrospinal fluid (CSF) in a ventriculo-peritoneal (VP) shunt in a hydrocephalus patient, and deployment of machine learning models to generate predictions for future CSF flow.

BACKGROUND

Hydrocephalus is a medical condition involving excess cerebrospinal fluid (CSF) in the brain. Hydrocephalus is often treated by surgically inserting a ventriculoperitoneal (VP) shunt inside a ventricle of the brain to divert CSF away from the brain and restore a normal flow and absorption of the CSF. The VP shunt is generally placed under the skin. Various medical complications can arise if the VP shunt malfunctions.

SUMMARY

The subject matter described herein is directed to remote detection of flowrate of cerebrospinal fluid (CSF) in a ventriculo-peritoneal (VP) shunt in a hydrocephalus patient to determine potential malfunctioning in drainage of the CSF from the brain. Additionally, machine learning is performed to generate predictions for future CSF flow, which can aid a clinician in treating hydrocephalus of that patient and/or other patients.

In general, in a first aspect, the disclosure features a method for monitoring a flowrate of cerebrospinal fluid (CSF) in a ventriculo-peritoneal (VP) shunt implanted in a human patient. The method includes: (i) receiving, at a device external to the human patient, data sensed by a plurality of sensors within the device and positioned relative to the VP shunt to drain excess cerebrospinal fluid from the human patient's brain; (2) determining, by the device and based on the sensed data, a rate of flow of the CSF in the VP shunt; and (3) transmitting (e.g., wirelessly), by the device, data indicating the rate of flow to a computing server.

Implementations of the method can include one or more of the following features and/or features of other aspects. For example, the method can further include transmitting the data indicative of the rate of flow to an application installed on a computing device coupled to the computing server. The computing server can be configured to transmit the data indicative of the rate of flow to the application in real-time.

In some implementations, the method further includes: receiving, by the device and from the computing server and in response to the transmitting the data indicating the rate of flow, instructions for adjusting the rate of flow in the VP shunt; and transmitting, by the device, instructions to electrical circuitry within the VP shunt, wherein the electrical circuitry within the VP shunt is configured to adjust the rate of flow in the VP shunt in accordance with the instructions. The electrical circuitry can adjust the rate of the flow in the VP shunt in real-time.

The device can include a first channel and a second channel, wherein the first channel overlays a portion of the VP shunt, wherein the second channel overlays a portion of human patient above their clavicle.

The sensors can include one or more of: at least one infrared sensor, at least one ultrasonic sensor, or at least one thermal sensor.

The computing server can be a cloud computing server. The computing server can be configured to perform operations including: deploying a machine learning model (or models) to generate predictions of future rate of flow of the cerebrospinal fluid; and transmitting (e.g., wirelessly) the predictions to an application installed on a computing device coupled to the computing server. The machine learning model(s) can be a supervised model, wherein the supervised model is a regression model or a classification model. The machine learning model(s) can include an unsupervised model, wherein the unsupervised model includes one or more of a clustering model and a dimensionality reduction model. The machine learning model(s) can be stored in the computing server. The machine learning model(s) can be stored in another computing server that is remote to the computing server.

The computing server can include: a normalization processor configured to communicate with the device, a software development kit configured to communicate with a first application installed on a computer configured to be operated by the human patient, and a web module configured to communicate with a second application installed on a computer configured to be operated by a clinician.

In general, in another aspect, the disclosure features a device for monitoring a flowrate of cerebrospinal fluid (CSF) in a ventriculo-peritoneal (VP) shunt implanted in a human patient. The device includes multiple sensors arranged in a housing configured to be placed external to the human patient above the VP shunt and generate signals responsive to a flow of the CSF in the VP shunt, a controller within the housing and configured to receive the signals from the plurality of sensors, wherein the controller is configured to determine, based on the signals, a rate of flow of the CSF in the VP shunt, and a communications transceiver to transmit data indicative of the rate of flow to a computing server.

Embodiments of the device can include one or more of the following features and/or features of other aspects. For example, the housing can defines a first channel and a second channel, the first channel being sized and shaped to overlay a portion of the VP shunt, the second channel being sized and shaped to overlay a portion of the human patient above their clavicle. The first and second channels can extend non-parallel to each other. For example, the first and second channels can extend perpendicular to each other.

The sensors can include one or more of: at least one infrared sensor, at least one ultrasonic sensor, or at least one thermal sensor.

In general, in another aspect, the disclosure features a non-transitory computer program product storing instructions that, when executed by at least one programmable processor, cause the at least one programmable processor to perform operations that include: receiving data sensed by a plurality of sensors within a device and placed above a ventriculo-peritoneal (VP) shunt implanted in a human patient and configured to drain excess cerebrospinal fluid (CSF) from the human patient's brain; determining, based on the sensed data, a rate of flow of the CSF in the VP shunt; and transmitting data indicating the rate of flow to a computing server. The subject matter described herein may provide one or more of the following advantages. For example, the device described herein can detect whether the VP shunt is potentially malfunctioning, which can cause an improper drainage, or stoppage of drainage, of the CSF from the brain. Data indicating potential malfunctioning of the VP shunt can be output (e.g., displayed) on applications (e.g., browser or native applications) on the patient's computer or a clinician's computer so that the problem with the VP shunt can be rectified. Further, the computing server described herein can deploy one or more machine learning models to predict future CSF flow, which can indicate to a clinician whether the VP shunt is expected to continue functioning properly as well as whether and when medical intervention may be needed. In some implementations, the drainage within the VP shunt may be automatically varied based on (a) data indicating VP shunt malfunction and/or (b) the predictions so as to automatically rectify the problems with the VP shunt. Such implementations can avoid complications due to internal blockage, over-drainage, under-drainage of VP shunt in hydrocephalus patients.

The details of one or more variations of the subject matter described herein are set forth in the accompanying drawings and the description below. Other features and advantages of the subject matter described herein will be apparent from the description, drawings, and claims.

DESCRIPTION OF DRAWINGS

Like reference symbols in the various drawings indicate like elements.

DETAILED DESCRIPTION

Figure 1:
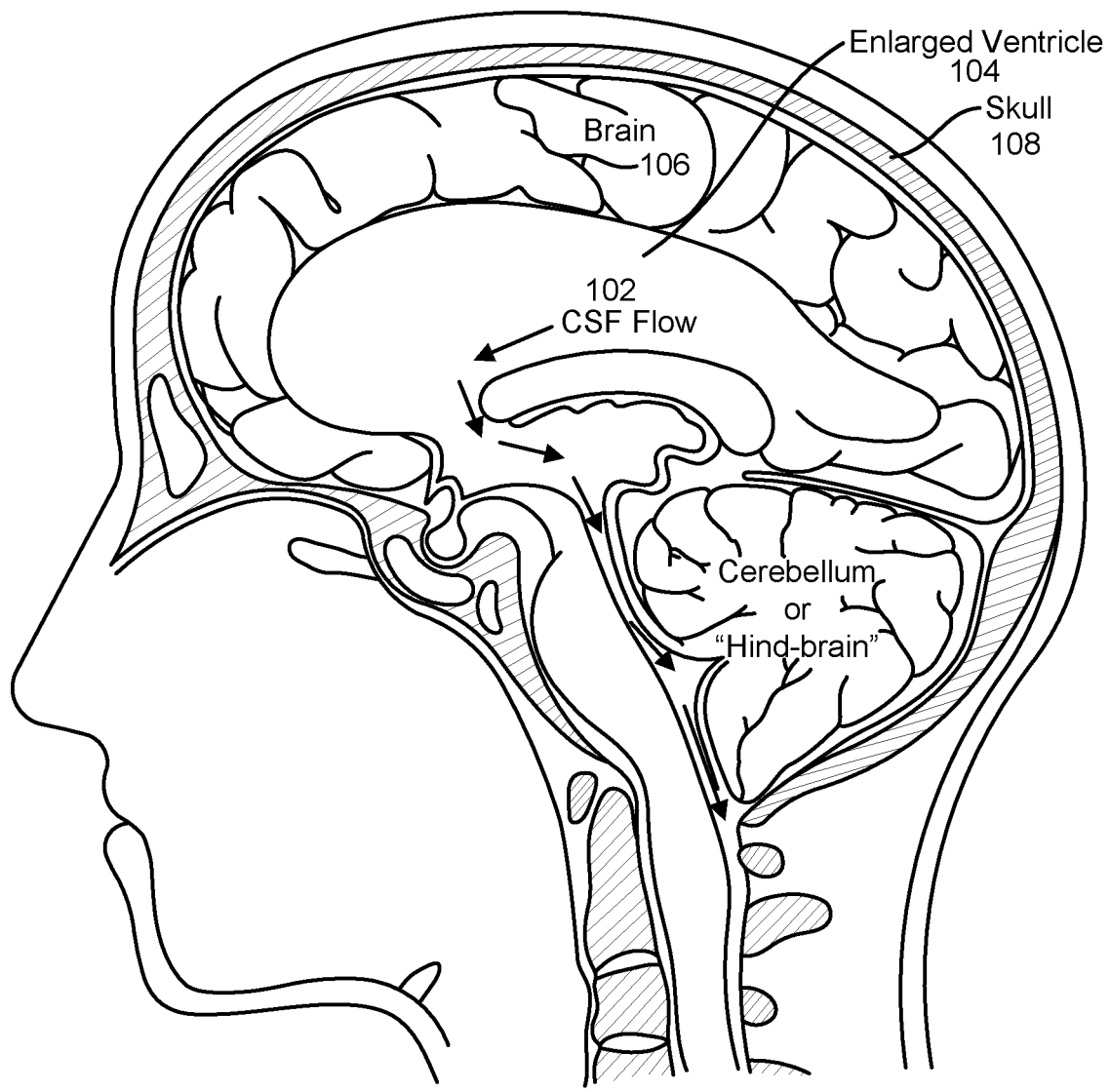
FIG. 1 illustrates a flow of cerebrospinal fluid (CSF) within a human body.

FIG. 1 illustrates a flow 102 of cerebrospinal fluid (CSF) within a human body. The majority of CSF is produced by the choroid plexus, which is a plexus of cells that arises from the tela choroidea in each of the ventricles 104 of the brain 106. The CSF moves through the ventricles 104, subarachnoid cisterns, and subarachnoid space. Subarachnoid cisterns are spaces formed by openings in the subarachnoid space. Subarachnoid space refers to locations around the brain 106 between the arachnoid membrane and the pia mater, through which major blood vessels pass. The CSF generally moves through the brain 106 and the spinal cord, and is soaked into the bloodstream. An example direction of the CSF flow is shown using arrows.

The choroid plexus in an adult can produce approximately 500 milliliters of CSF, around 135 milliliters of which is replaced every six hours as about that amount of CSF is reabsorbed by the body. The CSF levels in the brain can rise if (a) choroid plexus makes more than a normal amount (e.g., threshold amount) of CSF, (b) the CSF flow 102 is blocked due to, for example, cysts, tumors, or inflammation in the brain 106, (c) CSF does not get properly absorbed into blood, and/or the like. Such increase in CSF level in the brain 106 can push the brain 106 up against the skull 108, which can damage the brain tissue. One common condition caused by such increase in CSF level in the brain 106 is hydrocephalus, which is also sometime referred to as "water on the brain."

One example method of treating excess CSF in the brain 106, as occurs in hydrocephalus, is ventriculo-peritoneal (VP) shunting. VP shunting is a surgical procedure of inserting a VP shunt inside a ventricle 104 of the brain 106 to divert CSF away from the brain 106 and restore a normal flow and absorption of the CSF.

Figure 2:
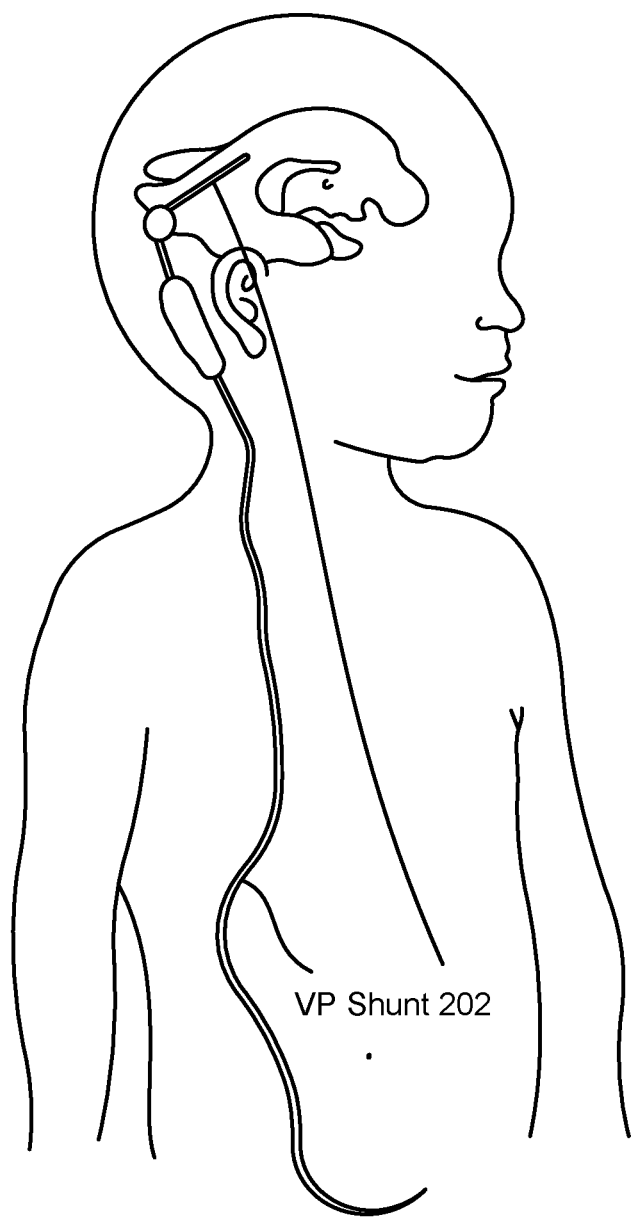
FIG. 2 illustrates a ventriculo-peritoneal (VP) shunt inserted inside a ventricle of the brain to divert (e.g., drain) CSF away from the brain and restore a normal flow and absorption of the CSF.

FIG. 2 illustrates a VP shunt 202 inserted inside a ventricle 104 of the brain 106 to divert CSF away from the brain 106 and restore a normal flow and absorption of the CSF. The VP shunt 202 is a thin tube through which excess CSF is drained to prevent pressure from getting too high (e.g., higher than a threshold value) in the brain 106. The shunt 202 is placed under the skin.

The VP shunt 202 includes a pump, activation and/or deactivation of which can be controlled remotely by a remote device, to pump out or drain out the excess CSF fluid. The remote device includes one or more arrays of one or more sensors to determine whether the CSF is in excess within the brain, and a controller that can control the activation or deactivation of the pump based on such determination of whether there is excess CSF in the brain 106. Although activation and deactivation of the pump of the shunt 202 is described as being controlled by the controller of the device, in some implementations the flow rate through the shunt can also be controlled by the controller of the device.

Figure 3:
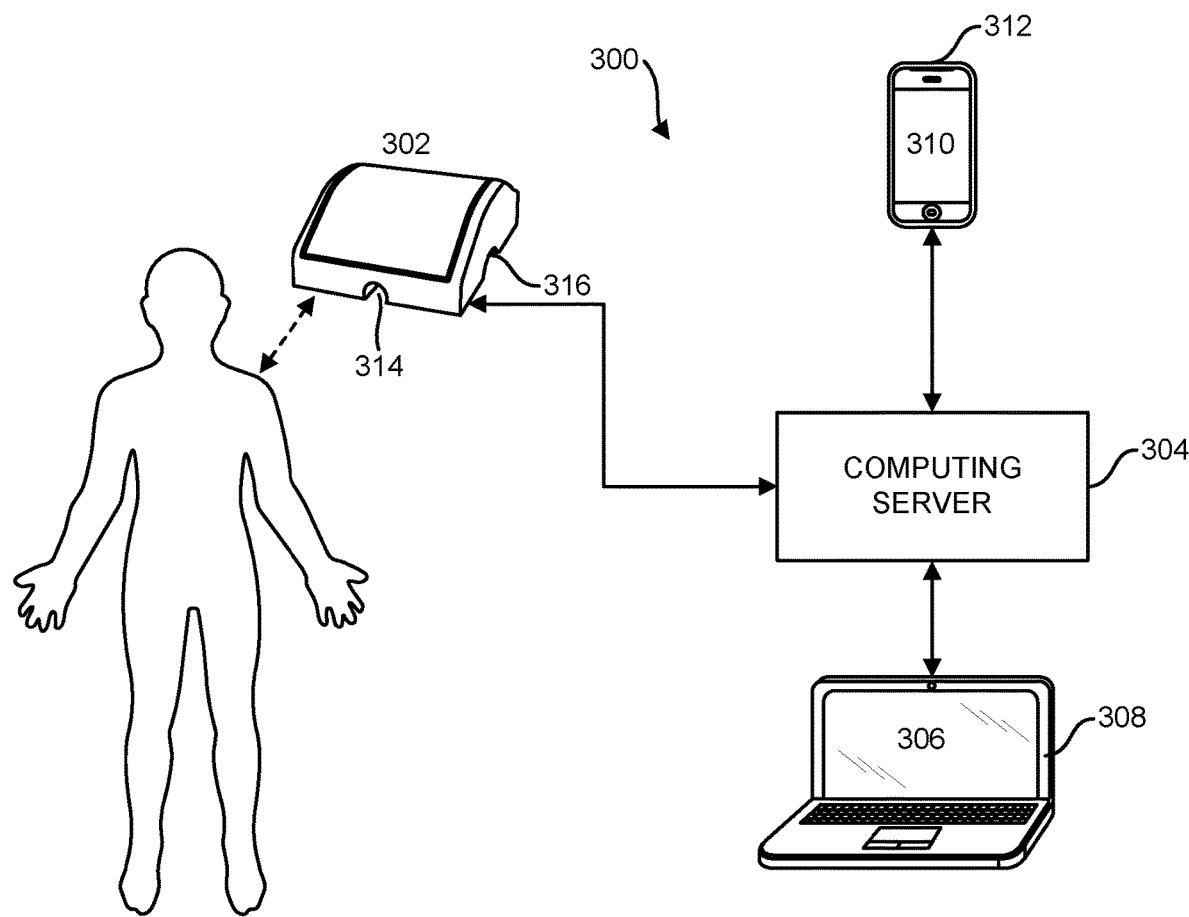
FIG. 3 illustrates an example system including a device to control the removal of excess fluid from the VP shunt, and a computing server that deploys one or more machine learning models using, as input, data collected by the device to generate predictions for future CSF flow.

FIG. 3 illustrates a system 300 including a device 302 to control the removal of excess fluid from the shunt 202, and a computing server 304 that deploys one or more machine learning models using, as input, data collected by the device 302 to generate predictions for future CSF flow 102. The computing server 304 can transmit the predictions to an application (e.g., browser or native application) 306 installed on a clinician computer 308, and such application 306 can output (e.g., display or generate an audio for) the predictions. Subsequent to, and/or in response to, the application 306 displaying the predictions, the clinician can use the application 306 to specify data to be presented to the patient. In some implementations, the data specified can be a selection or one or more predictions from multiple predictions made by the computing server 304. The computing server 304 can receive the data specified by the clinician, and present the data on an application (e.g., browser or native application) 310 installed on a patient computer 312.

Figure 10:
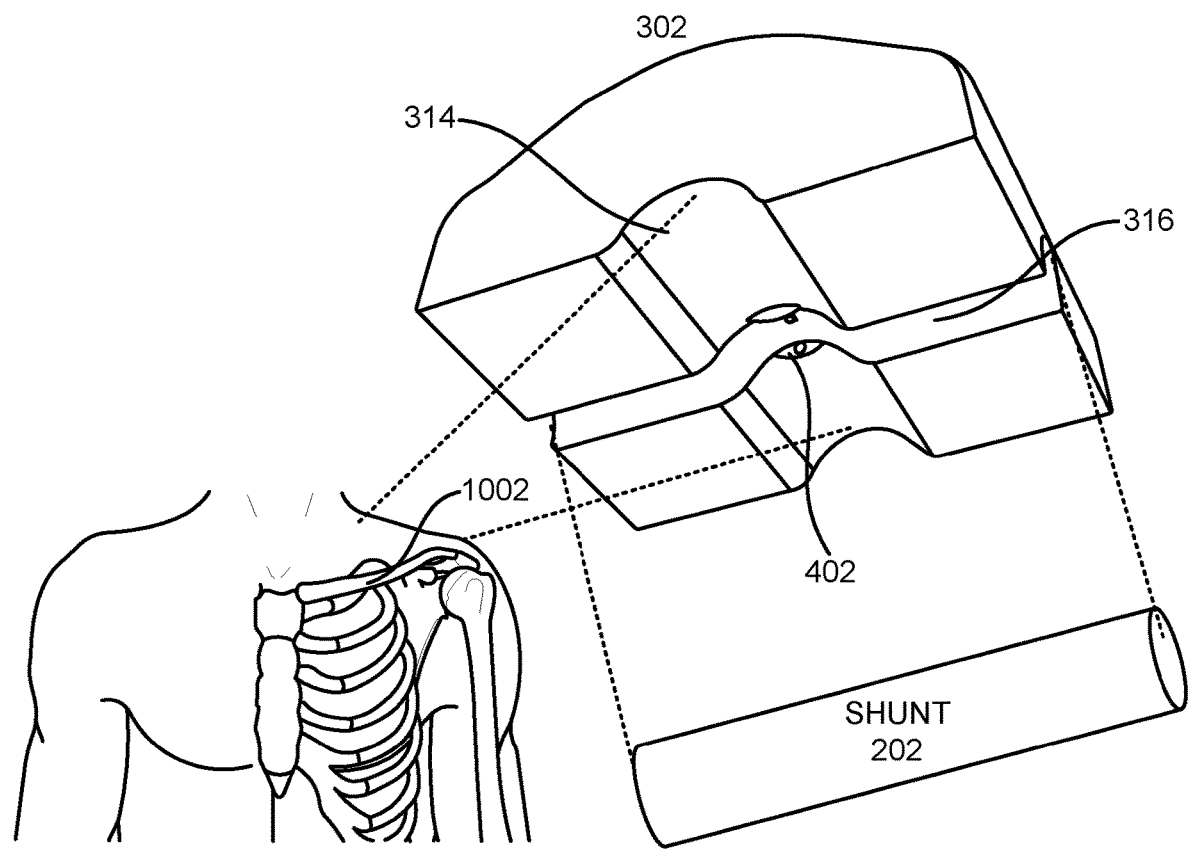

The device 302 includes a housing that is designed (e.g., shaped and sized) in a manner that it has two structures (e.g., channels) 314 and 316 at a bottom face which faces the patient during use. Each of the channels 314 and 316 can have a semi-cylindrical shape. The channel 314 is designed to be placed over a portion of the shoulder above the clavicle of the patient, as shown in FIG. 10. The channel 316 is designed to be placed over a portion of the VP shunt 202 that is adjacent to the clavicle of the patient. Generally, the channels are sized and shaped to accommodate the clavicle and VP shunt, respectively. In the shown implementations, the channels 314 and 316 can be perpendicular, assuming that VP shunt 202 is placed under the skin in a particular orientation where the axis of the portion of VP shunt 202 close to the clavicle is perpendicular to the length of the clavicle. In some implementations, the channels 314 and 316 can be at other angles with respect to each other so as to account for other respective angles between the axis of the portion of VP shunt 202 close to the clavicle and the length of the clavicle. Such other angles can be about 15 degrees, about 30 degrees, about 45 degrees, about 60 degrees, or about 75 degrees.

Figure 4:
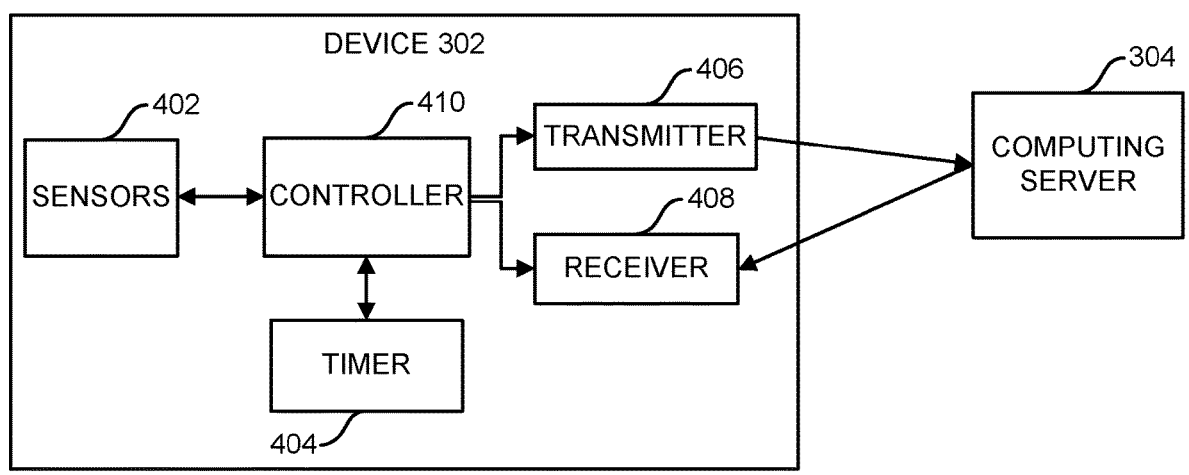
FIG. 4 illustrates some components within the device and communication of the device with the computing server.
Figure 11:
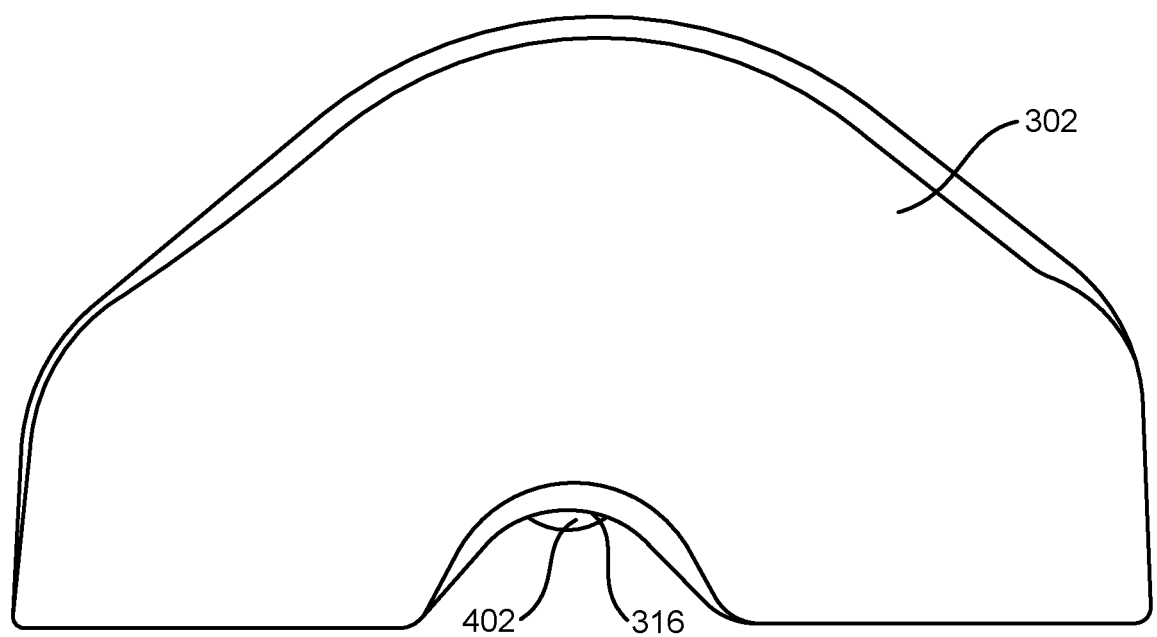
Figure 12:
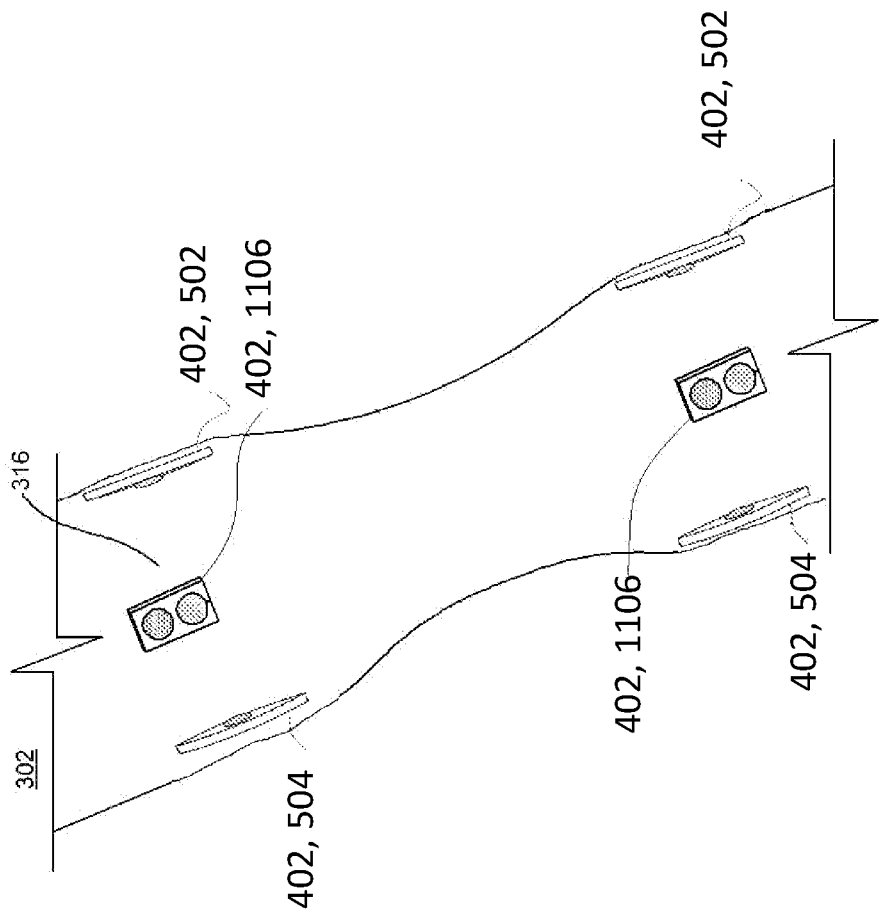

The device 302 includes components—such as sensors and electrical circuitry to determine whether the flow through the shunt is appropriate in order to determine whether the shunt is working properly (i.e., normally), controller that time-stamps data received from the sensors, and communication circuitry that facilitates communication with a remote computing server 304, as further described by FIG. 4—embedded on or attached to the inner surface of the channels 314 and/or 316 (as shown in FIGS. 10-12).

The computing server 304 can received time-stamped sensed data from the device 302. The computing server 304 can deploy one or more machine learning models to generate predictions. The predictions can be specific to the patient for which the data has been collected. In some implementations, the predictions can be for a category of patients, such as all patients that have one or more characteristics, such as particular race, gender, range of CSF in the brain, and/or the like. In certain implementations, the patients can also be categorized based on the amount of care each patient in a particular category needs, such as category of patients requiring minimal clinical care, patients requiring moderate clinical care, patients requiring frequent (e.g., more than a threshold level of frequency) clinical care, patients requiring immediate clinical care (e.g., patients currently admitted in a hospital), and/or the like.

The computing server 304 can input the data received from the device 302 to a trained machine learning model to generate the insights. The machine learning model may have been trained on historical sensed data, historical patient diagnosis, historical treatment, and/or other similar data of the patient and/or other patients with hydrocephalus and other characteristics within the same or similar category (e.g., same or similar one or more characteristics, such as race, gender, range of CSF in the brain, and/or the like) of patients. The machine learning model may have been trained previously by and/or on the computing server 304 and/or any other one or more devices.

The machine learning model that is trained and deployed to perform machine learning can be a supervised model (e.g., a model that involves learning a function that maps an input to an output based on example input-output pairs) or an unsupervised model (e.g., a model used to draw inferences and find patterns from input data without references to labeled outcomes). The supervised model can be a regression model (e.g., model where output is continuous) or a classification model (e.g., model where the output is discrete).

The regression model can be one or more of: (a) a linear regression model (e.g., a model that finds a line or curve that best fits the data), (b) a decision tree model (e.g., a model that has nodes, where the last nodes of the tree that are also referred to as leaves of the tree make decisions, where the number of nodes can be increased to enhance accuracy of the decision making and number of nodes can be decreased to enhance speed to reduce latency), (c) random forest model (e.g., model that involves creating multiple decision trees using bootstrapped datasets of the original data and randomly selecting a subset of variables at each step of the decision tree, where this model advantageously reduces the risk of error from an individual tree), (d) a neural network (e.g., a model that receives a vector of inputs, performs equations at various stages, and generates a vector of outputs), and/or the like.

The classification model can be one or more of: (a) a logistic regression model (e.g., a model that is similar to linear regression but is used to model the probability of a finite number of, e.g., two-outcomes; for instance, a logistic curve or equation may be created in such a way that the output values can only be between 0 and 1), (b) a support vector machine (e.g., a model that finds a hyperplane or a boundary between two classes of data that maximizes the margin or distance between the two classes), (c) naïve bayes model (e.g., a model that determines a class by implementing the bayes theorem).

The unsupervised learning models can be one or more of: (a) clustering models (e.g., a model that involves the grouping, or clustering, of data points, wherein such models can involve various clustering techniques such as k-means clustering, hierarchical clustering, mean shift clustering, and density-based clustering), and (b) dimensionality reduction models (e.g., a model that eliminates or extracts features to reduce the number of random variables under consideration by obtaining a set of principal variables), and/or the like.

The computing device 108 can implement (e.g., deploy) any of these machine learning models to generate predictions based on data received from the device 302.

FIG. 4 illustrates some components within the device 302 and communication of the device 302 with the computing server 304. The device 302 includes various electrical components including (a) one or more flow rate sensors 402 to detect flow rate of the CSF flow 102, (b) a timer 404, which time stamps the data sensed by the flow rate sensor, (c) a transceiver (i.e., transmitter 406 and receiver 408) to transfer the time-stamped sensed data to the computing server 304, and receive control instructions, (d) controller 410 to perform operations (e.g., activation or deactivation of the device 302 and/or any of the sensors 402) in response to the control instructions, and/or (e) memory (e.g., temporary storage, RAM, or the like) and/or databases to store the time-stamped sensed data before transmitting that data to the computing server 304 in batches (so as to optimize utilization of bandwidth). The sensors electrical components can be embedded in one or more electronic chips that can be attached to an inside surface of the channel 314 and/or the channel 316.

FIGS. 5-8 describe mechanisms that the device 302 can implement, individually or in any combination, to measure the rate of CSF flow within the VP shunt 202. The rate of CSF flow within the shunt can indicate whether the VP shunt 202 is continuing to appropriately treat hydrocephalus. If the VP shunt 202 is continuing to appropriately treat hydrocephalus, the computing server 304 can generate a notification to be output (e.g., displayed) on the application 306 and/or application 310.

Figure 5:
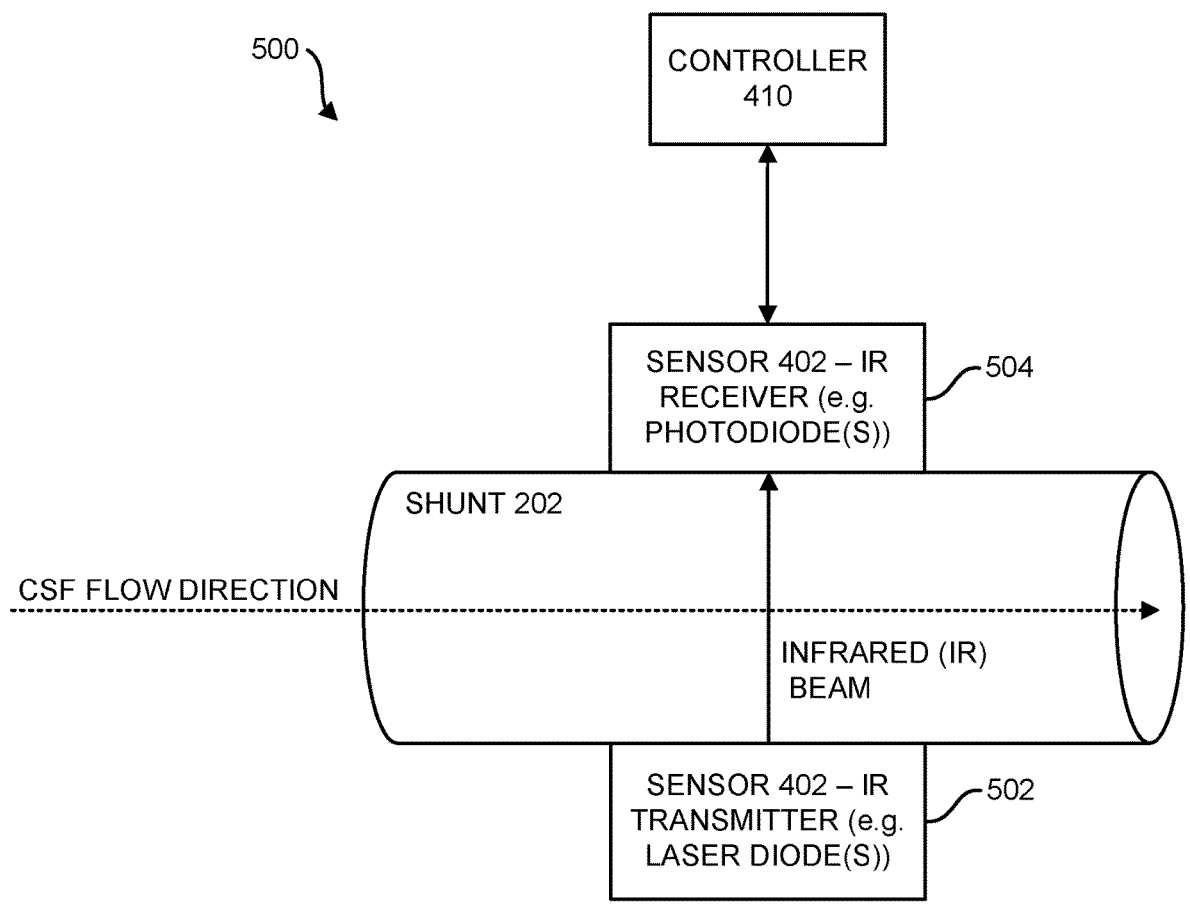
FIGS. 5-8 describe mechanisms that the device can implement, individually or in any combination, to measure the rate of CSF flow within the VP shunt.

FIG. 5 illustrates an implementation 500 where sensors 402 (more particularly, infrared sensors) are designed to be on inner surface of opposite ends of a cross-section of the channel 316. The sensors 402 here include an infrared transmitter (e.g., one or more laser diodes) 502 and an infrared receiver (e.g., one or more photodiodes) 504. The controller 410 can use the timer 404 to get time-stamped data sensed by the sensors 402, and use that data to determine the flow rate within the shunt 202.

Figure 6:
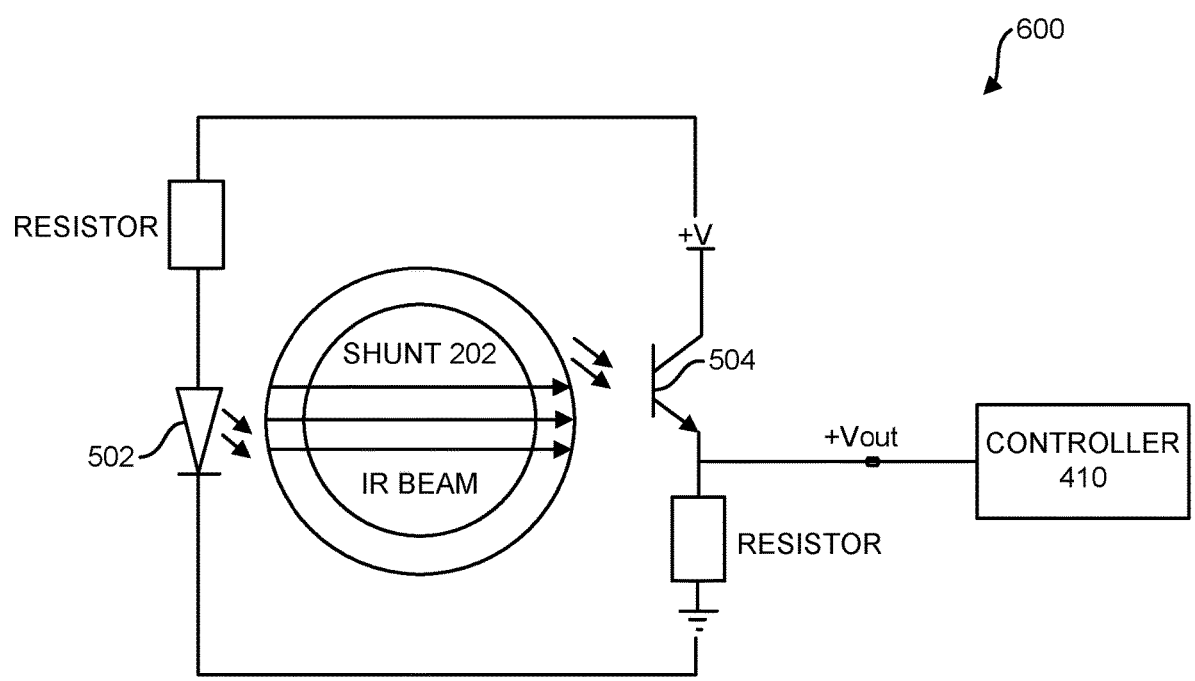

FIG. 6 illustrates an example of the implementation 500 of FIG. 5.

Figure 7:
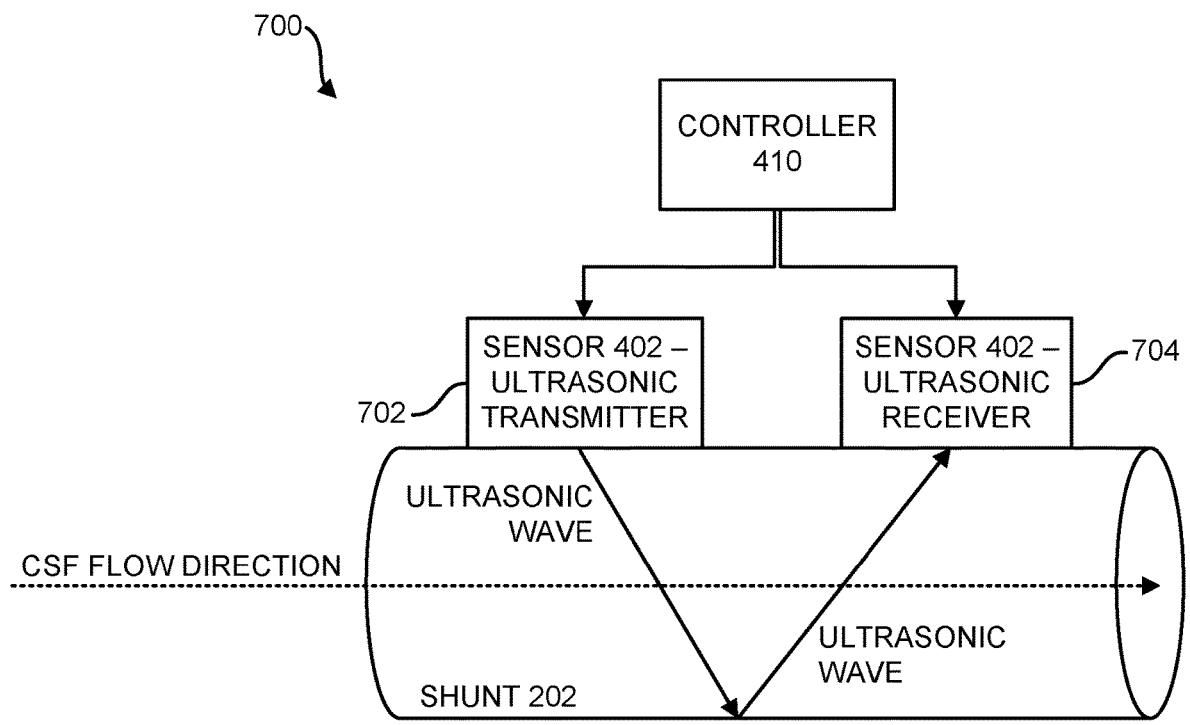

FIG. 7 illustrates an implementation 700 where sensors 402 (more particularly, ultrasonic sensors) are designed to be on inner surface, along a length of, the channel 306. The sensors 402 here include an ultrasonic transmitter 702 and an ultrasonic receiver 704. When there is no CSF flow within the VP shunt 202, the ultrasonic transmitter 702 sends ultrasonic waves that are bounced in the VP shunt 202 and received at the ultrasonic receiver 704; because there is no CSF movement, the frequency of the received signal is the same as the ultrasonic transmitter 702. Once the CSF flow starts in the shunt 202, the frequency of the ultrasonic waves received at the ultrasonic receiver 704 is either higher or lower (depending on the direction of the flow) than the one received when there was no CSF flow. The controller 410 can determine the flow rate of the CSF flow based on the difference between the frequency when there was CSF flow and the frequency when there was no flow.

Figure 8:
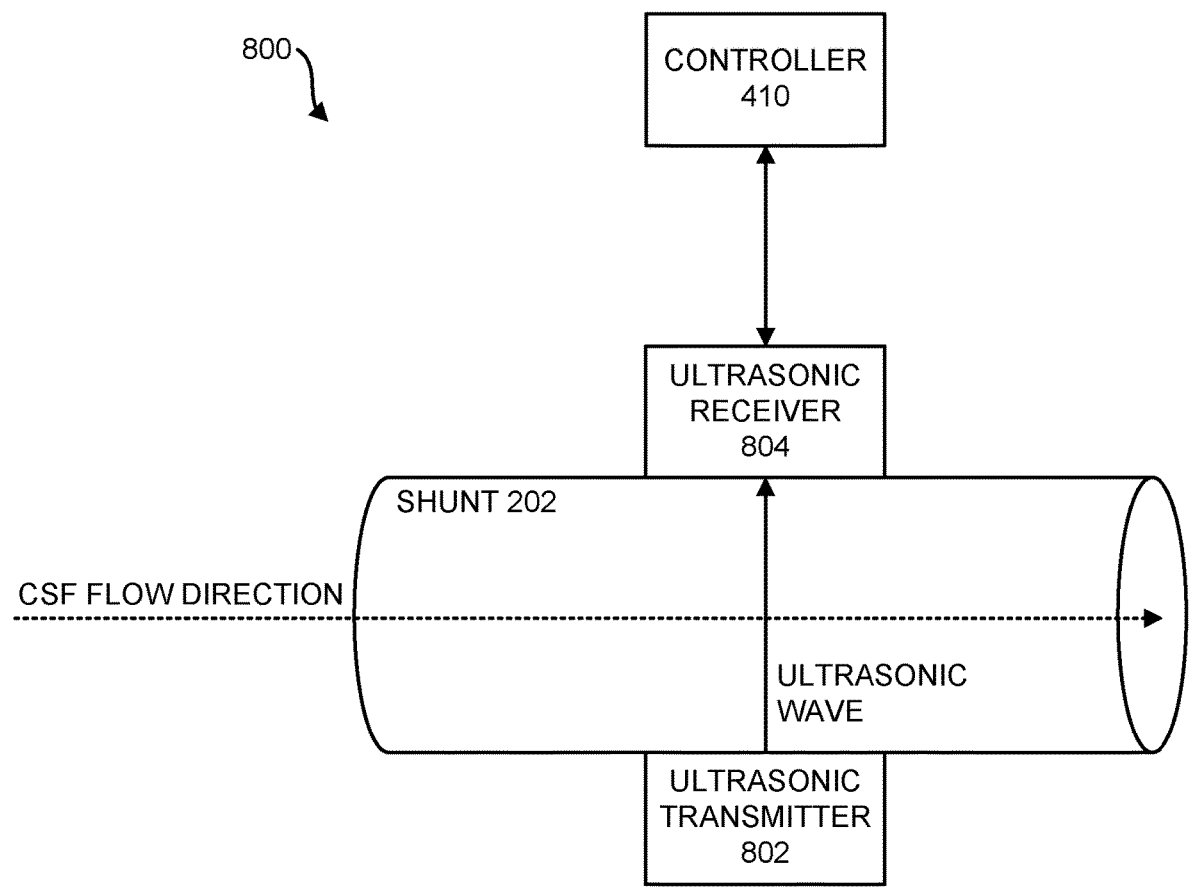

FIG. 8 illustrates an implementation 800 where sensors 402 (more particularly, ultrasonic sensors) are designed to be on inner surface of opposite ends of a cross-section of the channel 316. The sensors 402 here include an ultrasonic transmitter 802 and an ultrasonic receiver 804. The controller 410 can determine the flow rate of the CSF flow in the shunt based on the difference between the frequency when there was CSF flow and the frequency when there was no flow.

FIGS. 9-12 illustrate different views of the device 302.

Figure 9:
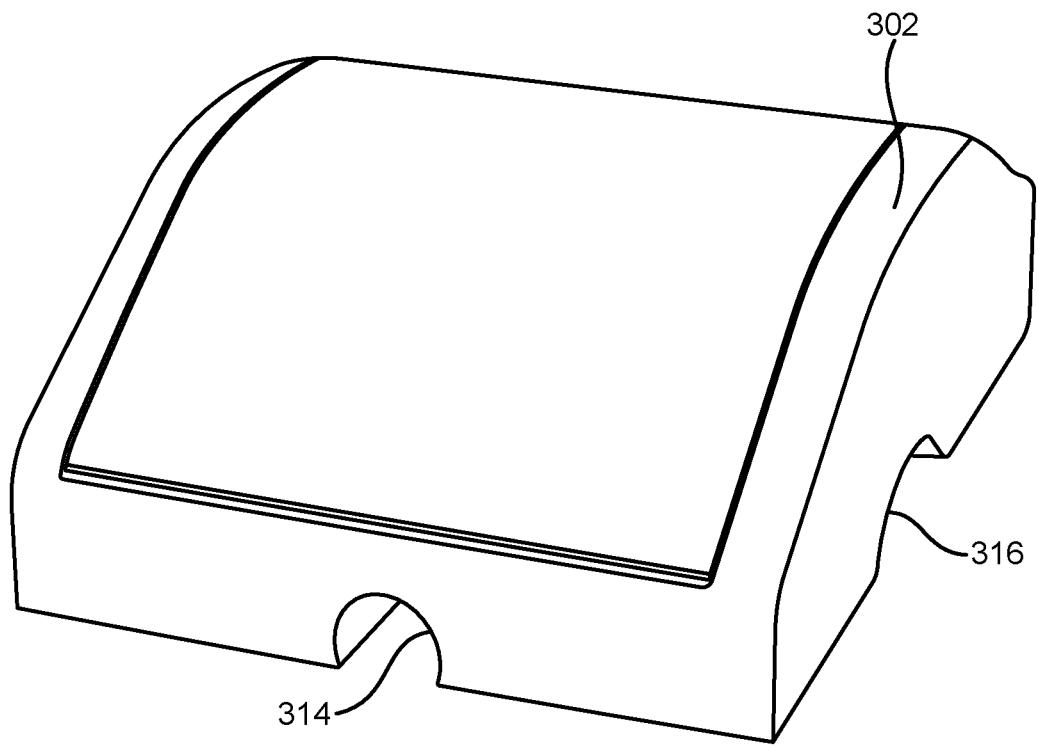
FIGS. 9-12 illustrate different views of the device.

FIG. 9 illustrates a closer top perspective view of the device 302.

FIG. 10 illustrates a bottom perspective view of the device 302. This drawing further shows, using dotted lines, that the device 302 housing is designed to firmly, yet comfortably, fit over the portion of shoulder above the clavicle 1002 and the shunt 202. The shunt 202 is designed to be under the skin, but is shown as outside the human body only for ease of reference to show the manner in which the channel 316 is designed.

In the shown implementation, the channels 314 and 316 can be perpendicular, assuming that VP shunt 202 and clavicle 1002 are perpendicular to each other. In some implementations, the channels 314 and 316 can be at other angles with respect to each other depending on the angle between the axis of the portion of VP shunt 202 close to the clavicle 1002 and the length of the clavicle 1002. Such other angles can, in various implementations, be 15 degrees, 30 degrees, 45 degrees, 60 degrees, or 75 degrees.

FIG. 11 illustrates a side view of the device 302.

FIG. 12 illustrates a bottom view of the device 302 showing sensors 402 attached to the inner surface of the channel 316. Two groups of sensors are arranged at different locations along the length of the channel 316. The sensor 1106 can be a thermal sensor 1106 that allows the temperature readings at different time points to be translated to the flow rate. Sensors 502 and 504 can be infrared transmitters and receivers, respectively, as described above. It can be advantageous to include several sensors on the device 302 to ensure accuracy of the sensed data, and in turn accuracy of the determined CSF flow rate, which indicates whether the VP shunt 202 is continuing to appropriately treat hydrocephalus. If the VP shunt 202 is continuing to appropriately treat hydrocephalus, the computing server 304 can generate a notification to be output (e.g., displayed) on the application 306 and/or application 310.

Figure 13:
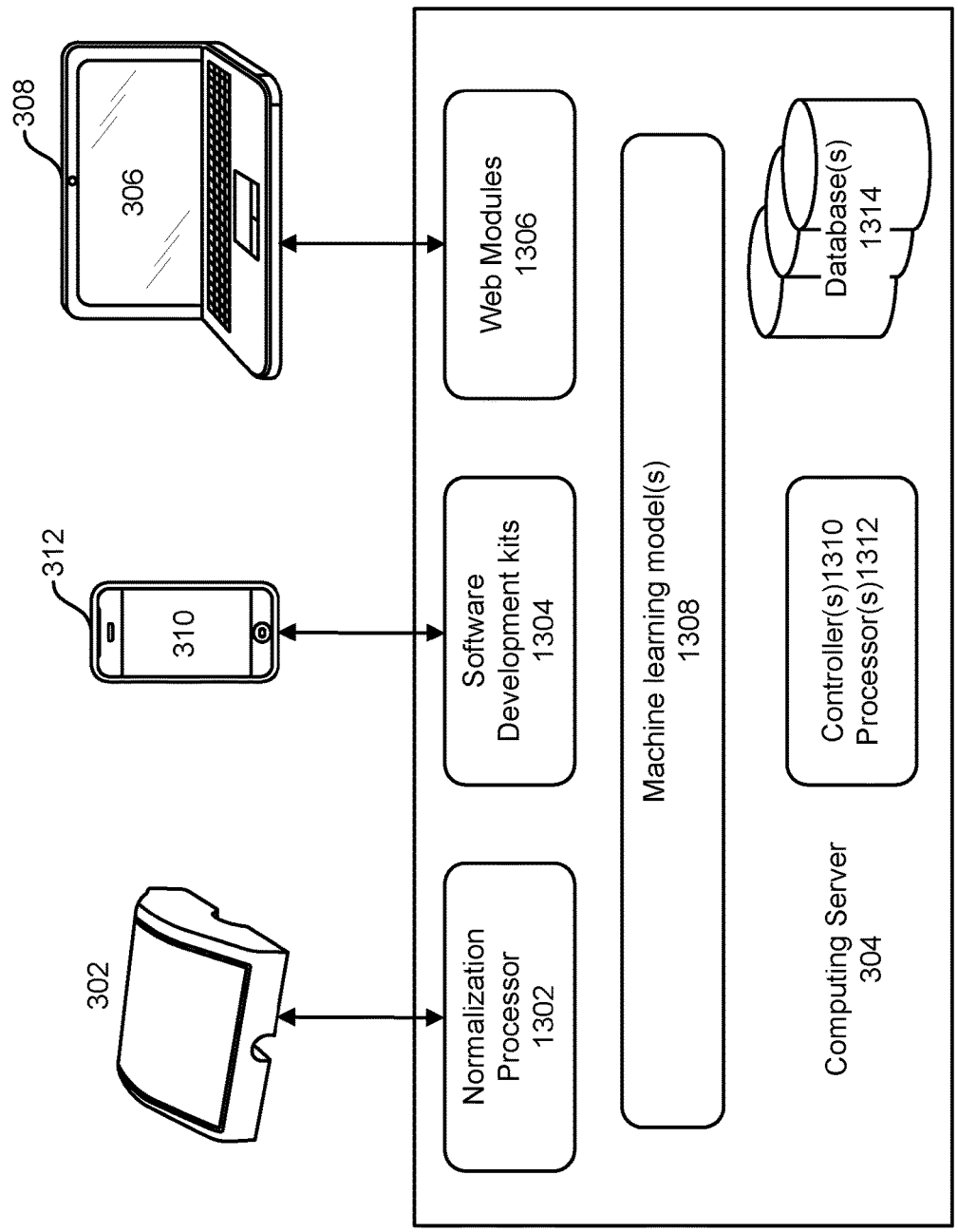
FIG. 13 illustrates various components of the computing server that communicates with device and applications.

FIG. 13 illustrates various components of the computing server 304 that communicates with device 302 and applications 306 and 310. The computing server 304 can be a cloud computing server. The cloud computing server 304 can include a normalization processor 1302, one or more software development kits (SDKs) 1304, one or more web modules 1306, one or machine learning models 1308, one or more controllers 1310 including one or more processors 1312, and one or more databases 1314 connected to the one or more controllers 1310.

The normalization processor 1302 can be configured to communicate with the device 302 via a first communication network. The one or more SDKs 1304 can be configured to communicate, via a second communication network, with the application 310. The one or more web modules 1306 can be configured to communicate, via a third communication network, with the application 306. Each of the first communication network, the second communication network, and the third communication network can be one or more of: local area network, internet, wide area network, metropolitan area network, BLUETOOTH network, infrared network, wired network, and any other communication network. In one implementation, the first communication network, the second communication network, and the third communication network may be the same network. In another implementation, the first communication network, the second communication network, and the third communication network may be different networks. In implementations where the communication device 312 is a laptop or a desktop computer, the application 310 can communicate with the web modules 1306. When the computing device 308 is a phone, a tablet computer or a phablet computer, the computing device 308 can communicate with the SDK 1304 in that case.

The one or more machine learning models 1308 that are trained and deployed to perform machine learning can be one or more supervised models (e.g., a model that involves learning a function that maps an input to an output based on example input-output pairs) or one or more unsupervised models (e.g., a model used to draw inferences and find patterns from input data without references to labeled outcomes). The one or more supervised models include a regression model (e.g., model where output is continuous) and/or a classification model (e.g., model where the output is discrete).

The regression model can be one or more of: (a) a linear regression model (e.g., a model that finds a line or curve that best fits the data), (b) a decision tree model (e.g., a model that has nodes, where the last nodes of the tree that are also referred to as leaves of the tree make decisions, where the number of nodes can be increased to enhance accuracy of the decision making and number of nodes can be decreased to enhance speed to reduce latency), (c) random forest model (e.g., model that involves creating multiple decision trees using bootstrapped datasets of the original data and randomly selecting a subset of variables at each step of the decision tree, where this model advantageously reduces the risk of error from an individual tree), (d) a neural network (e.g., a model that receives a vector of inputs, performs equations at various stages, and generates a vector of outputs), and/or the like.

The classification model can be one or more of: (a) a logistic regression model (e.g., a model that is similar to linear regression but is used to model the probability of a finite number of, e.g., two-outcomes; for instance, a logistic curve or equation may be created in such a way that the output values can only be between 0 and 1), (b) a support vector machine (e.g., a model that finds a hyperplane or a boundary between two classes of data that maximizes the margin or distance between the two classes), (c) naïve bayes model (e.g., a model that determines a class by implementing the bayes theorem).

The unsupervised learning models can be one or more of: (a) clustering models (e.g., a model that involves the grouping, or clustering, of data points, wherein such models can involve various clustering techniques such as k-means clustering, hierarchical clustering, mean shift clustering, and density-based clustering), and (b) dimensionality reduction models (e.g., a model that eliminates or extracts features to reduce the number of random variables under consideration by obtaining a set of principal variables), and/or the like.

Each database 1314 can be a cloud database, which can advantageously permit an easy scalability of the database 1314 when required (e.g., when additional data needs to be stored, which can happen, for example, when the number of patients increase beyond a threshold value). In one implementation, access to that database 1314 can be provided as a service. In some implementations, the database 1314 can be run on virtual machine instances. In one implementation, the database 1314 can be a disk storage. In some alternate implementations, the database 1314 can be a main memory (e.g., random access memory) rather than a disk storage. In those alternate implementations, access of data from the main memory can advantageously eliminate seek time when querying the data, which can provide a faster access of data, as compared to accessing data from the disk.

The use of a cloud computing server 304 can be advantageous over a traditional server, as the cloud computing server 304 permits a quick scalability by addition of additional web services within in a few seconds. When the load on the application 306 or application 310 increases, additional processors 1312 or databases 1314 can be added—or alternately the processing abilities of the existing processors 1312 or databases 1314 can be enhanced—within a few seconds. Additionally, inclusion of all of the normalization processor 1302, one or more SDKs 1304, one or more web modules 1306, one or more machine learning models 1308, at least one data processor 1312, and database 1314 within the cloud computing server 304 can advantageously enable: a dynamic provisioning, monitoring and managing of the applications 306 and 310; as well as a quick (e.g., within a few seconds) and easy restoring of any of those applications 306 or 310 to a previous version of those applications if and when required.

In some implementations, the controller computing server 304 can be communicatively coupled to a hardware accelerator to perform some machine learning computations. The hardware accelerator is computer hardware that allows performing some operations (e.g., calculations in the machine learning algorithms) more efficiently (e.g., more quickly) than possible in software running on a general-purpose central processing unit (CPU). Such efficiency in performing operations in hardware can decrease latency and increase throughput. The architecture with the hardware accelerator can offer additional advantages, including speedup (as compared to an architecture that does not use such hardware accelerator), reduced power consumption, lower latency, increased parallelism and bandwidth, better utilization of area and functional components available on an integrated circuit, and/or the like.

Figure 14:
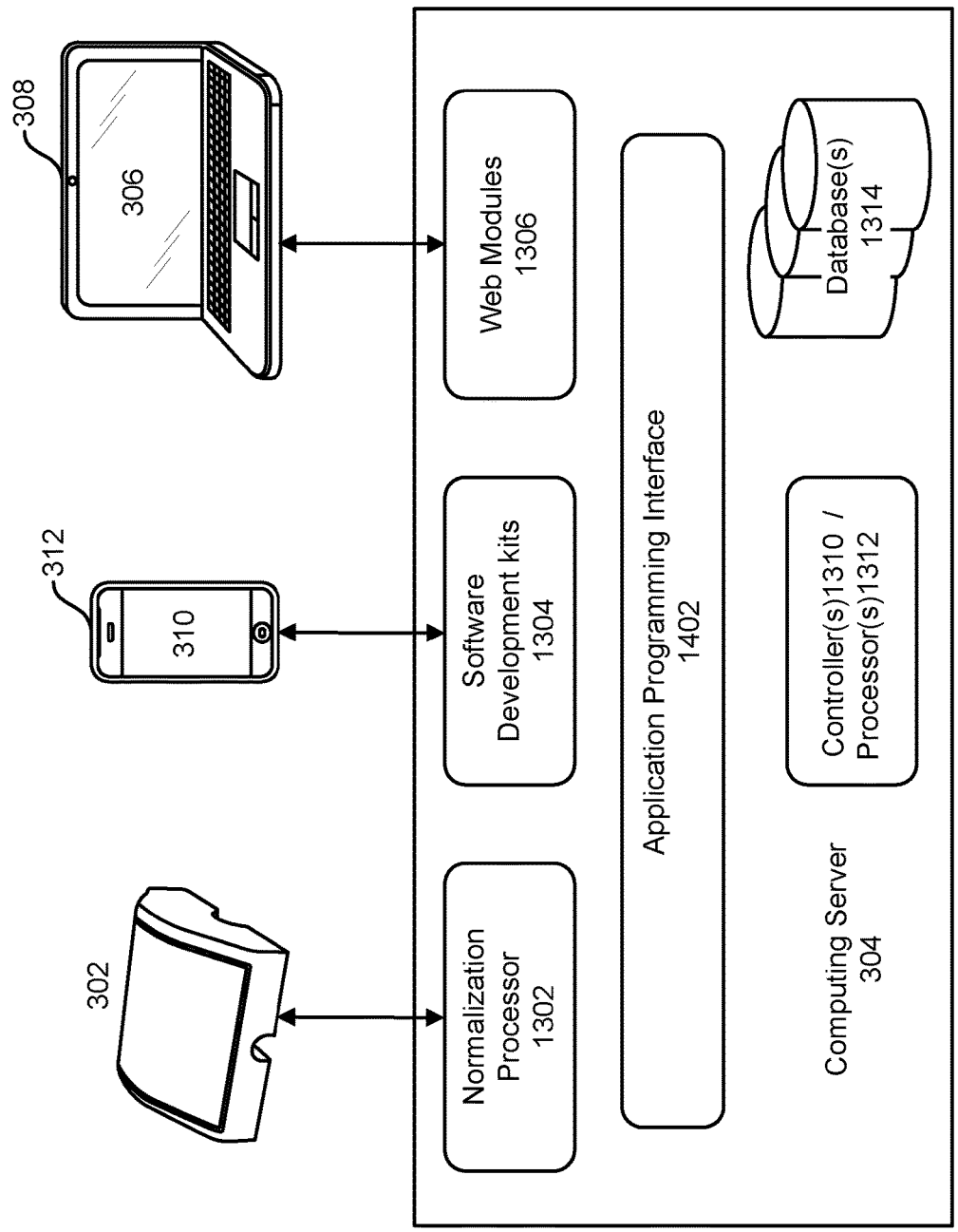
FIG. 14 illustrates a variation of the computing server of FIG. 13.

FIG. 14 illustrates a variation of the computing server of FIG. 13 that communicates with device 302 and applications 306 and 310. The computing server 304 can include an application programming interface 1402 that can facilitate communication with one or more machine learning models located at other servers that are remote from the computing server 304. In this manner, the computing server 302 may not need to have machine learning models resident on it, and the computing server 302 can utilize the machine learning models on a remote machine when required. Such architecture can allow the computing server 302 to run in a lean manner, which can improve computational speed.

The API 408 can be a set of subroutine definitions, protocols, and/or tools that define method of communication between the patient-application 108 and the computing server 110 and between the client-application 112 and the computing server 110. The API 408 can ensure, for example, that the data from the at least one of the normalization processor 402, the one or more SDKs 404, and the one or more web modules 406 can be read by the one or more controllers 410 and the one or more processors 412.

Figure 15:
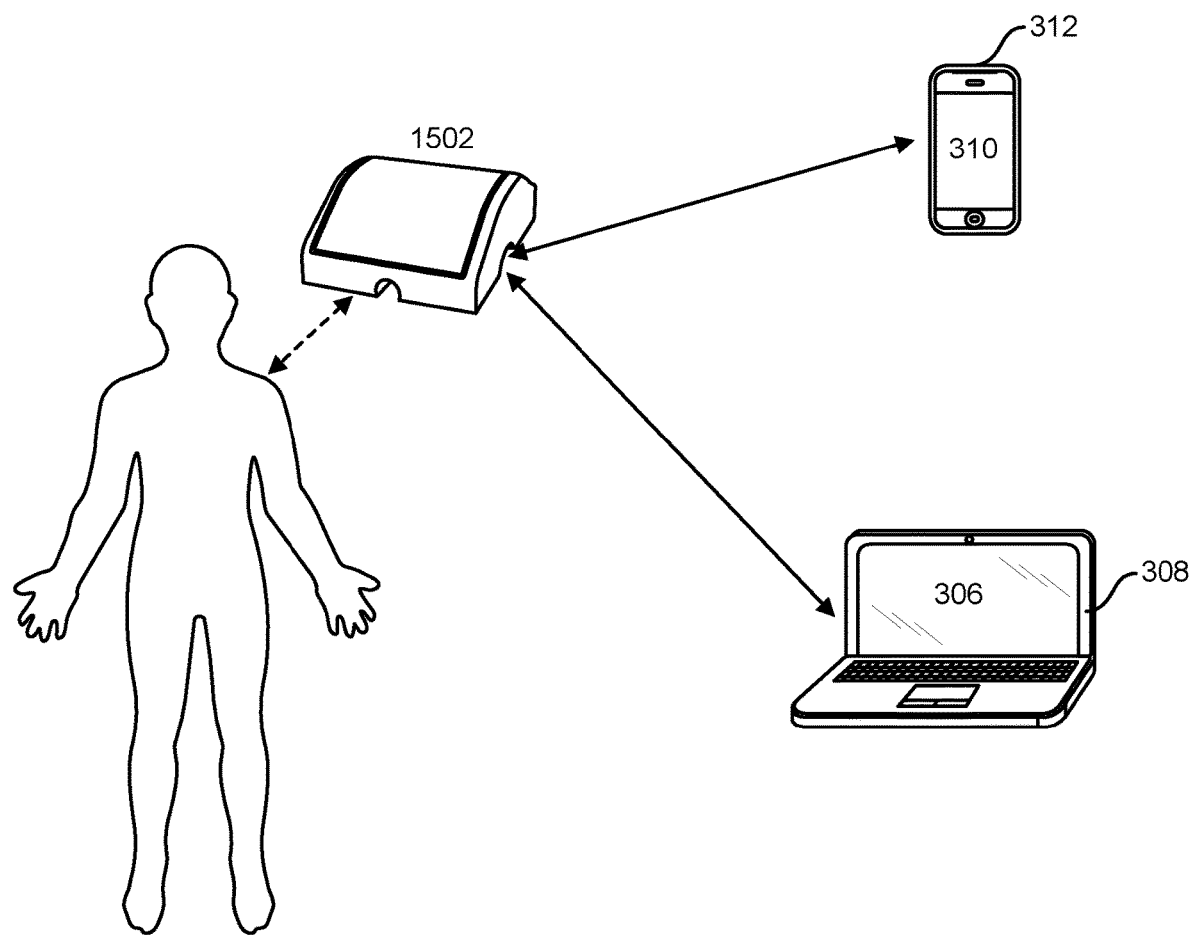
FIG. 15 illustrates a variation of the system of FIG. 3, where the device includes electrical circuitry within both the device and the computing server of FIG. 3 and performs operations of both the device and the computing server of FIG. 3.

FIG. 15 illustrates a system 1500, which can be a variation of the system 300 of FIG. 3, where the device 1502 includes electrical circuitry within both the device 302 and the computing server 304 and performs operations of both the device 302 and the computing server 304.

The subject matter and the actions and operations described in this specification can be implemented in digital electronic circuitry, in tangibly-embodied computer software or firmware, in computer hardware, including the structures disclosed in this specification and their structural equivalents, or in combinations of one or more of them. The subject matter and the actions and operations described in this specification can be implemented as or in one or more computer programs, e.g., one or more modules of computer program instructions, encoded on a computer program carrier, for execution by, or to control the operation of, data processing apparatus. The carrier can be a tangible non-transitory computer storage medium. Alternatively or in addition, the carrier can be an artificially generated propagated signal—e.g., a machine-generated electrical, optical, or electromagnetic signal—that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

The term "data processing apparatus" encompasses all kinds of apparatus, devices, and machines for processing data, including by way of example a programmable processor, a computer, or multiple processors or computers. Data processing apparatus can include special-purpose logic circuitry, such as a field programmable gate array (FPGA), an application specific integrated circuit (ASIC), or a graphics processing unit (GPU). The apparatus can also include, in addition to hardware, code that creates an execution environment for computer programs, e.g., code that constitutes processor firmware, a protocol stack, a database management system, an operating system, or a combination of one or more of them.

A computer program can be written in any form of programming language, including compiled or interpreted languages, or declarative or procedural languages; and it can be deployed in any form, including as a standalone program, e.g., as an app, or as a module, component, engine, subroutine, or other unit suitable for executing in a computing environment, which environment may include one or more computers interconnected by a data communication network in one or more locations.

A computer program may, but need not, correspond to a file in a file system. A computer program can be stored in a portion of a file that holds other programs or data, e.g., one or more scripts stored in a markup language document, in a single file dedicated to the program in question, or in multiple coordinated files, e.g., files that store one or more modules, sub programs, or portions of code.

The processes and logic flows described in this specification can be performed by one or more computers executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or both, or any other kind of central processing unit. Generally, a central processing unit will receive instructions and data from a read only memory or a random access memory or both. The essential elements of a computer are a central processing unit for executing instructions and one or more memory devices for storing instructions and data. The central processing unit and the memory can be supplemented by, or incorporated in, special-purpose logic circuitry.

Generally, a computer will also include, or be operatively coupled to, one or more mass storage devices, and be configured to receive data from or transfer data to the mass storage devices. The mass storage devices can be, for example, magnetic, magneto optical, or optical disks, or solid state drives. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

To provide for interaction with a user, the subject matter described in this specification can be implemented on one or more computers having, or configured to communicate with, a display device, e.g., a LCD (liquid crystal display) monitor, or a virtual-reality (VR) or augmented-reality (AR) display, for displaying information to the user, and an input device by which the user can provide input to the computer, e.g., a keyboard and a pointing device, e.g., a mouse, a trackball or touchpad. Other kinds of devices can be used to provide for interaction with a user as well; for example, feedback and responses provided to the user can be any form of sensory feedback, e.g., visual, auditory, speech or tactile; and input from the user can be received in any form, including acoustic, speech, or tactile input, including touch motion or gestures, or kinetic motion or gestures or orientation motion or gestures. In addition, a computer can interact with a user by sending documents to and receiving documents from a device that is used by the user; for example, by sending web pages to a web browser on a user's device in response to requests received from the web browser, or by interacting with an app running on a user device, e.g., a smartphone or electronic tablet. Also, a computer can interact with a user by sending text messages or other forms of message to a personal device, e.g., a smartphone that is running a messaging application, and receiving responsive messages from the user in return.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform the operations or actions. That one or more computer programs is configured to perform particular operations or actions means that the one or more programs include instructions that, when executed by data processing apparatus, cause the apparatus to perform the operations or actions. That special-purpose logic circuitry is configured to perform particular operations or actions means that the circuitry has electronic logic that performs the operations or actions.

The subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some implementations, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a sub-combination or variation of a sub-combination.

Similarly, while operations are depicted in the drawings and recited in the claims in a particular order, this by itself should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for monitoring a flowrate of cerebrospinal fluid (CSF) in a ventriculo-peritoneal (VP) shunt implanted in a human patient, the method comprising:
   receiving, at a device external to the human patient, data sensed by a plurality of sensors within the device and positioned relative to the VP shunt to drain excess cerebrospinal fluid from the human patient's a brain of the human patient;
   determining, by the device, a rate of flow of the CSF in the VP shunt by detecting a change in communications between each sensor of the plurality of sensors that monitor the CSF in the VP shunt, wherein detecting the change in the communications between each sensor of the plurality of sensors that monitor the CSF in the VP shunt comprises:
   determining a first frequency that is associated with a transmission from a first sensor to a second sensor matches to a second frequency of reception of the transmission by the second sensor, wherein the first frequency matches to the second frequency when no CSF flows in the VP shunt, wherein the first sensor is an ultrasonic transmitter, and the second sensor is an ultrasonic receiver;
   determining a third frequency associated with a second transmission from the first sensor to the second sensor differs from a fourth frequency of reception the second transmission by the second sensor, wherein the third frequency and the fourth frequency differ when the CSF flows in the VP shunt; and
   determining the rate of flow of the CSF in the VP shunt based on the difference between the first frequency and the third frequency;
   deploying one or more machine learning models to generate prediction of future rate of a flow of the cerebrospinal fluid;
   transmitting the predictions to an application installed on a computer device coupled to a computing server; and
   transmitting, by the device, data indicating the rate of flow to the computing server.

2. The method of claim 1, further comprising transmitting the data indicative of the rate of flow to an application installed on a computing device coupled to the computing server.

3. The method of claim 2, wherein the computing server is configured to transmit the data indicative of the rate of flow to the application in real-time.

4. The method of claim 1, further comprising:
   receiving, by the device and from the computing server and in response to the transmitting the data indicating the rate of flow, instructions for adjusting the rate of flow in the VP shunt; and
   transmitting, by the device, instructions to electrical circuitry within the VP shunt, wherein the electrical circuitry within the VP shunt is configured to adjust the rate of flow in the VP shunt in accordance with the instructions.

5. The method of claim 4, wherein the electrical circuitry adjusts the rate of the flow in the VP shunt in real-time.

6. The method of claim 1, wherein the device comprises a first channel and a second channel, wherein the first channel overlays a portion of the VP shunt, wherein the second channel overlays a portion of human patient above their clavicle.

7. The method of claim 1, wherein the plurality of sensors comprises one or more of: at least one infrared sensor, at least one ultrasonic sensor, or at least one thermal sensor.

8. The method of claim 1, wherein the computing server is a cloud computing server.

9. The method of claim 1, wherein the one or more machine learning models comprise a supervised model, wherein the supervised model is a regression model or a classification model.

10. The method of claim 1, wherein the one or more machine learning models comprise an unsupervised model, wherein the unsupervised model comprises one or more of a clustering model and a dimensionality reduction model.

11. The method of claim 1, wherein the one or more machine learning models are stored in the computing server.

12. The method of claim 1, wherein the one or more machine learning models are stored in another computing server that is remote to the computing server.

13. The method of claim 1, wherein the computing server comprises: a normalization processor configured to communicate with the device, a software development kit configured to communicate with a first application installed on a computer configured to be operated by the human patient, and a web module configured to communicate with a second application installed on a computer configured to be operated by a clinician.

* * * * *